(12) United States Patent
Frielinghaus et al.

(10) Patent No.: US 12,413,682 B2
(45) Date of Patent: Sep. 9, 2025

(54) REAL TIME AUGMENTATION

(71) Applicant: Brainlab SE, Munich (DE)

(72) Inventors: Nils Frielinghaus, Heimstetten (DE); Markus Neff, Ottobrunn (DE)

(73) Assignee: Brainlab SE, Munich (DE)

( * ) Notice: Subject to any disclaimer, the term of this patent is extended or adjusted under 35 U.S.C. 154(b) by 181 days.

(21) Appl. No.: 18/019,417

(22) PCT Filed: Aug. 7, 2020

(86) PCT No.: PCT/EP2020/072309
§ 371 (c)(1),
(2) Date: Feb. 2, 2023

(87) PCT Pub. No.: WO2022/028718
PCT Pub. Date: Feb. 10, 2022

(65) Prior Publication Data
US 2023/0276016 A1    Aug. 31, 2023

(51) Int. Cl.
*H04N 5/265* (2006.01)
*G06T 7/20* (2017.01)
*G06V 10/74* (2022.01)

(52) U.S. Cl.
CPC ............ *H04N 5/265* (2013.01); *G06T 7/20* (2013.01); *G06V 10/761* (2022.01);
(Continued)

(58) Field of Classification Search
CPC ....... A61B 1/0005; A61B 34/20; A61B 34/25; A61B 2090/365; A61B 90/37;
(Continued)

(56) References Cited

U.S. PATENT DOCUMENTS

2005/0182295 A1*   8/2005   Soper ................... A61B 1/2676
                                                          600/117
2013/0176336 A1    7/2013   Hannula
(Continued)

FOREIGN PATENT DOCUMENTS

CN    106797451 A    5/2017
CN    108027652 A    5/2018
(Continued)

OTHER PUBLICATIONS

Bensch, Alexander Maxwell. Toward Real-Time Video-Enhanced Augmented Reality for Medical Visualization and Simulation. Rochester Institute of Technology (Year: 2015).*
(Continued)

*Primary Examiner* — Xin Sheng
(74) *Attorney, Agent, or Firm* — Gray Ice Higdon

(57) ABSTRACT

A computer-implemented method of generating an overlay of medical video data and overlay data is presented. The method comprising the steps acquiring, from a medical video modality, the medical video data comprising at least a first video frame and a second video frame of different points in time, t1 and t2, (step S1), analysing the acquired medical video data comprising a comparison of the video data captured by the first and the second video frames (step S2); providing initial overlay data (step S3), generating modified overlay data by adapting the initial overlay data based on a result of the analysis of the medical video data (step S4), and generating the overlay by generating a video output comprising at least medical video data originating from the medical video modality and comprising the generated modified overlay data (step S5). In a particular embodiment, the determined change over time in the first and second video frames is a spatial shift of an object imaged in the video frames.

15 Claims, 3 Drawing Sheets

(52) U.S. Cl.
CPC .............. *G06T 2207/10056* (2013.01); *G06T 2207/10068* (2013.01); *G06T 2207/10132* (2013.01); *G06V 2201/07* (2022.01)

(58) Field of Classification Search
CPC ........... G06T 7/0012–0016; G06T 7/20; G06T 2207/10056; G06T 2207/10068; G06T 2207/10132; G06T 2207/30004; G06T 2210/41; G06V 10/761; G06V 2201/07; H04N 5/265
See application file for complete search history.

(56) References Cited

U.S. PATENT DOCUMENTS

| | | | |
|---|---|---|---|
| 2014/0118398 A1* | 5/2014 | Hall | ............... G06T 9/00 345/633 |
| 2014/0275760 A1 | 9/2014 | Lee et al. | |
| 2016/0249989 A1* | 9/2016 | Devam | ............... A61B 5/024 345/633 |
| 2018/0042680 A1 | 2/2018 | Dimaio | |
| 2018/0228555 A1 | 8/2018 | Charron | |
| 2019/0015163 A1 | 1/2019 | Abhari | |
| 2019/0247130 A1* | 8/2019 | State | ............... A61B 34/20 |
| 2019/0247131 A1 | 8/2019 | Hoffman | |
| 2019/0357982 A1* | 11/2019 | Flossmann | ............. A61B 34/25 |
| 2020/0388075 A1* | 12/2020 | Kazanzides | ............. A61B 90/37 |

FOREIGN PATENT DOCUMENTS

| | | | |
|---|---|---|---|
| DE | 102017010351 | 5/2019 | |
| DE | 102018113047 | 12/2019 | |
| EP | 2091241 | 8/2009 | |
| EP | 2632382 | 9/2013 | |
| EP | 3328305 B1 * | 3/2019 | ............. A61B 34/20 |
| WO | 2018206086 | 11/2018 | |
| WO | 2018235533 | 12/2018 | |
| WO | WO2021037381 | 8/2019 | |

OTHER PUBLICATIONS

European Patent Office, Extended European Search Report issued in Application No. 24186078.2, 5 pages, dated Sep. 27, 2024.
International Search Report and Written Opinion issued for Application No. PCT/EP2020/072309, 10 pages, dated May 4, 2021.
The State Intellectual Property Office of People's Republic of China, First Office Action issued in Application No. 202080104146.4, 21pages, dated Mar. 21, 2025.
European Patent Office, Extended European Search Report issued in Application No. 25165844.9, 6 pages, dated Jun. 5, 2025.

* cited by examiner

REAL TIME AUGMENTATION

FIELD OF THE INVENTION

The present invention relates to real time augmentation, in particular it relates to a computer-implemented method of generating an overlay of medical video data and overlay data, to a computer program, to a non-transitory program storage medium storing such a program and to a computer for executing such a program, as well as to a medical video modality system.

TECHNICAL BACKGROUND

Diagnostic medical procedures often involve the use of cameras to visualize anatomical structures, which are difficult or even impossible to see with the naked eye. In such cases, cameras help in visualizing those anatomical structures by being placed in the vicinity of those structures with an unobstructed line of sight and by transmitting the received images to a remote display or monitor that can be easily observed by a medical practitioner. For example, endoscopic procedures utilize cameras to examine and visualize the interior of hollow organs or cavities within a patient's body. Common endoscopes have an elongated instrument body with a distal section that is usually placed within the patient's body, and a proximal section that usually remains outside the patient's body. While the distal endoscope section is provided with at least one camera, the entire endoscope body can be held in place by a support structure which connects to the proximal section of the endoscope and which may be motorized, such that a medical practitioner can move the endoscope together with the camera to a desired location by controlling the motorized structure via a user interface.

The applicant of the present application, Brainlab AG, has developed and acquired a technology comprising a stand-alone box that is able to forward video signals in real-time and which can branch off in real-time a video signal for recording and/or processing the video signal. In this context, Brainlab AG acquired the technology developed by the Ayoda GmbH, which had filed the published patent application DE 10 2017 010 351 A1. This patent application describes a meanwhile well-known technology for overlaying video signals in high definition and in real-time.

The inventors of the present invention have found that during the use of for example an endoscope, the medical practitioner always needs the live video image of the endoscope, since otherwise the controlling of the medical procedure is difficult. Every time delay between a movement of the endoscope and the displayed video images would cause an irritation for the medical practitioner. The inventors of the present invention have also found that it would be very beneficial in such situations to provide further image information for the medical practitioner in form of an augmentation, i.e. an overlay.

Hence, the present invention has the object of improving the display of medical video data to the user.

The present invention can be used for and in medical video data processing and medical video data imaging, e.g. in connection with a system such as the one described in detail in DE 10 2017 010 351 A1.

Aspects of the present invention, examples and exemplary steps and the embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given, which shall not be understood to limit the invention only to the features or a combination of the features described in this section.

The disclosed method comprises the acquisition of at least two video frames from a medical video modality, like for example an endoscope, an ultrasonic device, a microscope or any combination thereof. Of course, also other medical video modalities may be used. In this method, these video frames are compared to each other, wherein this comparison can be embodied in many different ways, as will be described in the context of particular embodiments hereinafter. For example, in one embodiment, a drift detection is carried out in the sense that the influence of a motion between the video modality and the image object is determined/calculated. In another exemplary embodiment, the comparison of the two video frames captured by the medical video modality is embodied as automatically determining a landmark of an augmentation model in the first video frame and is embodied as searching and finding said determined landmarks in the second video frame. The respective results of these two exemplary embodiments of said "comparison" described hereinbefore, can then be used during further steps of the method, in which initial overlay data are modified based on the result of said comparison between the first and second video frame. This modification of the initial overlay data represents the generation of modified overlay data, which are then displayed together with medial video data from the medical video modality to the medical practitioner. The combination of the modified overlay data and the medical video data, which combination is displayed to the user as the video output, is called herein "overlay" and is understood by the skilled reader as the desired augmentation.

This computer-implemented method of generating an overlay of medical video data and overlay data can be carried out on a computer or on a calculation unit, as is disclosed herein. However, the method may also be carried out in a medical video modality system, which comprises such an imaging system for generating said medical video data. Exemplary embodiments of such imaging devices are endoscopes, ultrasonic devices, microscopes, and any combination thereof. It must also be noted that the device described in patent application DE 10 2017 010 351 A1 can be used to implement the method described herein. The inventors of the present invention have found that the local processor, calculation unit or local intelligence of such a device can be beneficially used to optimize the latency of an overlay signal. In particular, medical video modality systems using field programmable gate arrays (FPGA) often do have a lot of calculation capacity, which can be used for optimizing such a generation of an overlay.

In particular embodiments, the inventors of the present invention suggest to calculate an extrapolation of the initial overlay data, i.e. the augmentation data, based on an analysis of said first and second video frames. In such an embodiment, the first and second video frames that were acquired from the medical video modality are analysed with respect to changes in their video content. The change of the video content determined from the comparison between the first and second video frames can then be used in this embodiment to calculate the extrapolation of the initial overlay data to a particular point in time in the future. The provided initial overlay data, which in an exemplary embodiment are realized as an augmentation model of e.g. a part of the imaged body of a patient, are extrapolated to this later point in time in the future. Hence, in this embodiment, the present invention suggests analysing the change of the video signal in the past, extrapolates this signal to a particular point in time in the future and then morphs the initial overlay data into the correct, i.e. the corresponding, form. This embodiment is, for example, realized in the detailed embodiment shown in FIG. 3.

As indicated before, in a second embodiment of the present invention, the analysis of the first and second video frames acquired from the medical video modality are compared in the sense that an automatic determination of one or more landmarks of an augmentation model in the first video frame is carried out followed by a searching and finding step of said determined landmark within the second video frame. This embodiment will be described in more detail in the context of the embodiment shown in FIG. 4.

It should be noted, that the used initial overlay data may be of several different nature and origins. In particular, such initial overlay data may be a video signal from a medical tracking system, but may also be for example an augmentation model that is stored in an external database and that is retrieved or at least accessible by the device or system carrying out the presented method.

As will become apparent to the skilled reader from the present disclosure, the overlay that can be generated with the present invention is a real-time overlay in the sense that it has a very short latency in time compared to the medical video data. In particular, a latency of below one video frame or even a latency of below a few pixels of a video frame can surprisingly be achieved. In addition, this reduction in latency achievable with the present invention will be described and elucidated with more detailed embodiments hereinafter.

GENERAL DESCRIPTION OF THE INVENTION

In this section, a description of the general features of the present invention is given for example by referring to possible embodiments of the invention.

According to a first aspect of the present invention, a computer-implemented method of generating an overlay of medical video data and overlay data is presented. The method comprises the step of acquiring in step S1, from a medical video modality, the medical video data comprising at least a first video frame and a second video frame of different points in time, t1 and t2. The method further comprises in step S2 an analysis of the acquired medical video data, which comprises carrying out a comparison of the video data captured by the first and the second video frames. As was already indicated before, such a comparison of the captured video data of both video frames can be carried out in several different manners, as will be explained in more detail hereinafter. Moreover, initial overlay data are provided in step S3 and modified overlay data are generated by adapting the initial overlay data based on a result of the analysis of the medical video data, i.e., based on result of the comparison of the video content of the first and second video frames, i.e. step S4. Moreover, the computer-implemented method comprises the step of generating the overlay by generating a video output comprising at least medical video data originating from the medical video modality and comprising the generated modified overlay data, i.e. step S5.

As has been described before, the present invention can be carried out by several different embodiments of comparing the captured video data of the first and second video frame and of generating the overlay being a video output comprising at least medical video data originating from the medical video modality and the generated modified overlay data. However, all such embodiments allow for the generation of an overlay in real-time, i.e. having a latency in time compared to the medical video data of below one video frame, or particularly having a latency compared to the medical video data of only a few pixels of a video frame, e.g. below twenty pixels of a video frame, below eight pixels of a video frame, or even below four pixels of a video frame. This will become apparent from the following disclosure.

Note that the low latency of the present invention is achieved, inter alia, by not reading a complete video frame and then subsequently processing it, but rather directly processing and putting out each pixel or a small subgroup (2, 4, 8) of consecutive pixels right after it is read from the input. The processing can e.g. be the blending of the input color with an overlay image that includes color and opacity information, which is simultaneously read from memory. During this reading, a known shift of the overlay can be accounted for. Alternatively, the processing could consist of blending with a textured triangular model thereby interpolating the color and opacity from the texture on-the-fly.

It should be noted that the initial overlay data as well as the generated modified overlay data can be static data, but can also be dynamic data in the sense that it changes over time.

It must be noted, that in the context of the present invention, of course more than the recited first, second and third video frames can be used to carry out the present invention.

The computer-implemented method presented herein can be carried out by FPGA based hardware. For a particular implementation, one may exemplarily use the system described in said aforementioned German patent application.

According to an exemplary embodiment of the present invention, the step of analysing the acquired medical video data comprises determining a change in the medical video data over time by comparing the first and the second video frame. Note that a change in the video content within these two video frames is determined. The method further comprises the step of acquiring, from the medical video modality, at least a third video frame of a third point in time t3. The step of generating the modified overlay data (step S4) furthermore comprises the use of the determined change in the video data of the first and second video frames over time in the calculation that is carried out by the method. Thus, the determined change in the video frames is used for calculating an extrapolation of the initial overlay data to the point in time t3 (step S4a). Moreover, the generation of the overlay (step S5) furthermore comprises the generation of the video output, which comprises the third video frame and the initial overlay data that were extrapolated to the third point in time t3, i.e. the modified overlay data, (step S5a).

It must be noted, that a particular further development of the aforementioned embodiment is described in the context of FIG. 3. Several different opportunities exist to determine said change in the content of the medical video data over time. The most basic example is to determine the translation of an object that was imaged in the first video frame and is imaged in the second video frame at other coordinates, since a movement has happened between the points in time t1 and t2 at which the first and the second video frames were acquired. Determining said change of the object position in the first and second video signal and using said detecting translation of the object is understood by the skilled practitioner as determining an influence of a motion between the imaging device of the video modality and the imaged object. This determined change in the medical video data can then be used to compensate for the influence of the motion that has happened when generating the modified overlay data. Such a determined translation of an object in the first and second video frame is also referred to herein as shift detection or shift analysis. However, also rotations or zooms that describe the change between the first and the second video frame can be detected automatically with the method of the present invention, according to other embodiments. But also a distortion, an increase in size of an object, a decrease in size of an object can be automatically determined by a corresponding image processing algorithm used in this embodiment.

For example, the method of "optical flow" known to the skilled practitioner can be used for determining said change in the medical video data over time. In order to determine the direction and/or the velocity of motion of the video image across the screen, i.e. of the motion of image features or objects between the first video frame and the second video frame, any conceivable image processing techniques known in the art can be applied. For example, the "optical flow" of the displayed image content can be determined as well as the "ego motion" of the camera with respect to the environment observed by the camera. Further, any techniques based on edge- and/or feature-detection as well as any techniques based on image-comparison may be used in the context of the present invention.

A comparison of the image content between the first and second video frame allows determining the motion the camera of the medical video modality has actually performed. For example, an overall motion vector can be calculated on the basis of a positional difference of at least one, preferably of a plurality of features in the at least two images obtained. In a specific case, when all or almost all recognizable features have moved between two obtained images by the same amount and in the same direction, i.e. described by the same motion vector within the displayed image plane, it can be assumed that the camera has been moved translatory and substantially perpendicularly to the camera's line of sight. If, in another case, the camera has been rotated about its line of sight, the recognizable features seen in both obtained video frames will describe a vector-field around a center point that represents the camera's center of rotation within the image plane. If, in still another exemplary case, the video frame/image features as seen in the obtained video frames describe a vector-field with the specific vectors converging to or diverging from a specific center point, it can be assumed that the camera is moved towards or away from an observed object along the camera's line of sight. Of course, an actual motion of the camera during a medical procedure can be superimposed by any conceivable combination of the above described exemplary motions.

In summary, the present invention makes use of at least two video frames obtained by the medical video modality to determine a motion the camera has actually performed between the compared video frames.

Further, the inventive method may consider directions of motion which are parallel and perpendicular (i.e. "zoom in"- and "zoom out"-directions with respect to the image plane) to the plane of the images received by the medical video modality.

Instead of such a movement detection by means of e.g. "optical flow" as described hereinbefore, also anatomical landmarks could be detected in the video frames. Another alternative for analysing the acquired medical video data is to identify markers, which are attached to medical instruments, which are displayed in the first and second video frame. It is of course possible to use also an additional, external system, like an optical tracking system, which detects the presence of such a marker or markers and which provides the data about said marker positions to the device/system carrying out the method. However, as will be appreciated by the skilled practitioner, also other methods for analysing the acquired medical video data to then accordingly adapt the initial overlay data can be used in the context of the present invention.

As was described before, several different possibilities of analysing a change in the first and second video frame can be used. This analysis may entail determining a vector or a vector field that describes an underlying movement between the scene imaged in video frame 1 and video frame 2. However, this may also determine six degrees of freedom, i.e. three translational and three rotational degrees of freedom, describing the movement of an imaged object or of the imaged scene in front of a calibrated camera. In particular embodiments, an additional zoom factor may be taken into account. It is thus possible to detect drifts and/or rotations, movements of instruments, movement of the camera and movements of the imaged object with particular embodiments of the present invention.

In an embodiment, the initial overlay data is an augmentation model and the determined change in the video data over time is used for calculating the extrapolation of this augmentation model to the point in time t3, i.e. the morphing of said model to the point in time t3. The system carrying out this embodiment of the present invention then generates the video output, which comprises the third video frame and the initial overlay data that were extrapolated to the third point in time t3, i.e. the modified overlay data. In other words, said extrapolated initial overlay data are the modified overlay data that are generated by the method present herein.

The augmentation model might consist of a bitmap, preferably with color and opacity information, or a point cloud, a wireframe, a (e.g. triangular) surface model (preferably with a color opacity texture), a volumetric model or any other graphical model that can be rendered in real time. In addition to the graphical information, the augmentation can comprise information on how it is adapted e.g. how a determined shift or a 6-D transformation or a zoom factor is to be applied or potential anchor landmarks that are detected in the video frame and used to define the transformation of the model to the actual overlay.

Furthermore, the augmentation model may for example be an image and the corner points of the image are adapted, or the augmentation model may be a line model or a surface model (triangles and/or squares) and the nodes of this model are adapted. In another embodiment, a textured model, preferably using an additional transparency channel, could be newly rendered when adapting the augmentation model based on the result of the analysis of the first and second video frame, as has been explained hereinbefore in detail. In an embodiment, a so-called sweep line method is used in which the complexity of the model is reduced such that the maximum number of cross-sections of a line with the edges of the model do not exceed a particular and constant number that has been previously defined. The system carrying out the present invention may pre-order the data that are processed during the invention, preferably a pre-ordering in direction of the vertical axis of the image is used. As has been described before in detail, a stop or cancellation criterion could be defined such that no augmentation, i.e. no overlay generation, takes place when the detected movement is that significant that an augmentation would not provide fruitful results or would not be technically feasible.

According to an exemplary embodiment of the present invention, the relation t1<t2<t3 holds true for said first, said second and said third video frames. In this embodiment, the third video frame is preferably directly following the second video frame in the video stream of the medical video modality.

In this embodiment, the relation between the three points in time is defined and only preferably, and thus necessarily limiting this embodiment, that the third frame can directly follow the second video frame.

According to another exemplary embodiment of the present invention, the determined change over time in the first and the second video frames is a spatial shift of an object imaged in the video frames.

In other words, this embodiment explains that from the two video frames, a shift in space, i.e. a movement of the imaged object in the coordinate system of the imaging device has taken place. This movement is detected automatically by the computer-implemented method of this embodiment using, for example, an image processing algorithm.

According to another exemplary embodiment of the present invention, the initial overlay data is an augmentation model. This augmentation model may be stored in the device carrying out this method or may also be retrieved via a data connection with an external data storage like a server on which the augmentation model is stored. Moreover, the step of the generation of the modified overlay data (step S5) comprises at least one of applying a spatial shift to the augmentation model, applying a distortion to the augmentation model, newly rendering the augmentation model, adapting one or more parameters of the augmentation model, replacing the augmentation model by another augmentation model.

Based on the comparison of the first and second video frame, it is determined in this computer-implemented method how the initial overlay data, i.e. the initial augmentation model, must be adapted in order to be usefully overlaid with the video stream to the user. This embodiment describes several possibilities how the augmentation model can be adapted when it is morphed to the current point in time. Such morphing of the anatomical model will be described in more detail in the particular embodiments described in the context of FIGS. 3, 4 and 5.

According to another exemplary embodiment of the present invention, the method further comprises the step of calculating an influence of a motion between an imaging device of the medical video modality and the imaged object and compensating for said calculated influence when generating the modified overlay data.

In other words, this embodiment looks at the influence of motion between the imaged scene and the video device by comparing the first and second video frames and compensates for such a movement or movements by adapting the initial overlay data correspondingly. The adaption of the initial overlay data can be realized in many different ways, e.g. by spatial shift to the initial overlay data, applying a distortion to the initial overlay data, newly rendering the initial overlay data, adapting parameters of the initial overlay data, replacing the initial overlay data by other overlay data, and any combination thereof.

According to another embodiment of the present invention, the extrapolation of the initial overlay data is calculated to a fourth point in time t4 and the generation of the video output comprises the third video frame and the initial overlay data extrapolated to the fourth point in time t4. Moreover, between the third and fourth video frame from t3 and t4, a latency in time exists that is below one video frame, below one line of a video frame, or below 10, 8, 5 or below 4 pixels of a video frame of said video modality.

In one embodiment described before, the initial overlay data are extrapolated to the time t3 of the third video frame, which is used in the overlay that is displayed to the user. However, in this embodiment using said "calculation to a fourth point in time t4", the augmentation model, or in general the initial overlay data, are extrapolated even more, since it takes into account an additional latency that is present between the video frame t3 and the generation of the overlay at t4. This latency is, however, below one video frame, or below one line of a video frame or below a few pixels of a video frame, Hence, the corresponding time in seconds that has to be added from t3 to t4, i.e. said very low latency mentioned just before, can be used for extrapolating the augmentation model/initial overlay data. The augmentation model extrapolated to t4 can then be beneficially displayed together with the video frame of t3 to the user.

According to another exemplary embodiment of the present invention, the comparison of the video data captured by the first and the second video frames is carried out as an automatic determination of at least one landmark of an augmentation model in the first video frame and comprises searching and finding said determined landmark in the second video frame.

This landmark detection is realized e.g. in the exemplary embodiment shown in FIG. 4. Automatic image analysis software may be used for scanning, for example, a first video frame of the medical video modality and particular landmarks of an augmentation model may be identified in there. Such identified landmarks can then be searched for in the second video frame, which corresponds to an analysis of landmarks in real-time. This will be explained in more detail hereinafter in the context of FIG. 4.

According to an exemplary embodiment of the present invention, the method comprises the step of determining from the first video frame an augmentation model and determining from the first video frame at least one landmark of said determined augmentation model. The method then automatically identifies said determined at least one landmark in the second video frame while reading out the second video frame. At least one parameter of the augmentation model is adapted in this method based on the result of the landmark identification in the second video frame. In this way, the modified overlay data are generated. In other words, the modified overlay data are the augmentation model with the at least one parameter being adapted. Moreover, the step of generating the overlay (step S5), which overlay is shown to the medical practitioner as video output comprising the second video frame and the adapted augmentation model (step S10). Moreover, the landmark identification (step S8) and the adaption of the at least one parameter of the augmentation model (step S9) are carried out simultaneously with the generation of the overlay (step S5), i.e. within the same video frame. In a preferred embodiment, the generation of the overlay is carried out simultaneously, i.e. within the same video frame, with the read out of the second video frame.

According to another exemplary embodiment of the present invention, the step of landmark identification (step S8) comprises the step of evaluating whether a particular landmark determined in the first video frame is present in the second video frame within a pre-defined maximum number of video frame pixels thereby using a (e.g. triangular) video frame read-out. Moreover, in this embodiment, no overlay is generated if said particular landmark is not present/cannot be detected or found in the second video frame within said maximum number of video frame pixels.

In other words, the presented method or algorithm of this embodiment waits until enough information has been gathered about the second video frame and only then decides whether an overlay is generated or not. In other words, a maximal delay, i.e. the predefined maximum number of video frame pixels, is pre-defined in this embodiment and an augmentation is carried out only if within these maximum number of video frame pixels the corresponding landmark is detected during the read out of said video frame. If no such corresponding landmark is detected or found by the algorithm, no augmentation is provided to the user, i.e. no overlay is generated. In other words, the augmentation in real-time is carried out as long as the change in the video frames is below a certain threshold. According to a preferred embodiment thereof it is indicated to the user, for example by an audio and/or video signal, that no augmentation is currently provided.

According to another exemplary embodiment of the present invention, the method comprises the steps of determining a spatial drift of an object imaged by the medical video modality by analysing at least two video frames of said video modality from points in time before said second video frame was captured. Moreover, it is decided, based on the determined spatial shift, preferably by the amount of the determined shift, whether a landmark is accepted to be used in the method and/or whether the overlay is generated.

In other words, the overlay is switched on or off depending on the amount of drift or depending on the drift speed that has been detected/determined by analysing the first and the second video frame. This method of switching on and off the overlay may also be dependent on the position of the landmarks that were automatically determined in the first video frame and that are searched and found in the second video frame, as has been described hereinbefore in another embodiment.

According to another exemplary embodiment of the present invention, the method comprises the step of automatically identifying a particular instrument in the first video frame and acquiring an augmentation model of said identified particular instrument from a database thereby providing the initial overlay data.

In this embodiment, the presented method analyses in real-time landmarks within a video frame acquired from the medical video modality. While the pixels of said video frame are read out it is determined by the device carrying out the presented method which augmentation model, i.e. which initial overlay data, is/are to be used. Known software for identifying said particular medical instrument in the video frame can be applied by the skilled practitioner. Moreover, the system/device carrying out this embodiment may then access an internal data storage unit or may also access a database that is somewhere remote from the system/device carrying out the presented method. In any case, the provided augmentation model is adapted based on the real-time analysis of the first video frame, in which the particular instrument was identified. Based on this identification, the adapted augmentation model is displayed together with the video frame to the user.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. The invention may alternatively or additionally relate to a (physical, for example electrical, for example technically generated) signal wave, for example a digital signal wave, carrying information which represents the program, for example the aforementioned program, which for example comprises code means which are adapted to perform any or all of the steps of the method according to the first aspect. A computer program stored on a disc is a data file, and when the file is read out and transmitted it becomes a data stream for example in the form of a (physical, for example electrical, for example technically generated) signal. The signal can be implemented as the signal wave which is described herein. For example, the signal, or the signal wave is constituted to be transmitted via a computer network, for example LAN, WLAN, WAN, for example the internet. The invention according to the second aspect therefore may alternatively or additionally relate to a data stream representative of the aforementioned program. In a third aspect, the invention is directed to a non-transitory computer-readable program storage medium on which the program according to the fourth aspect is stored.

In a fourth aspect, the invention is directed to at least one computer (for example, a computer), comprising at least one processor (for example, a processor) and at least one memory (for example, a memory), wherein the program according to the fourth aspect is running on the processor or is loaded into the memory, or wherein the at least one computer comprises the computer-readable program storage medium according to the fifth aspect.

According to a third aspect of the present invention, a medical video modality system is presented, which comprises the at least one computer on which the before mentioned program is running or where the program mentioned before is loaded into the memory of the computer. The medical video modality system further comprises a medical imaging device for generating the medical video data.

In an embodiment thereof, the medical video modality system of the present invention is provided in combination with a navigation system or a surgical navigation system as described in detail herein below.

In a preferred embodiment thereof, the medical video modality system comprises an imaging device comprising an endoscope, an ultrasonic device, a microscope, or any combination thereof.

Definitions

In this section, definitions for specific terminology used in this disclosure are offered which also form part of the present disclosure.

Computer Implemented Method

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Acquiring Data

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Marker

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

Marker Device

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows determining the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

Navigation System

The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information.

Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

Surgical Navigation System

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

Landmarks

As is clear to the skilled reader, in the context of the present intervention, the term landmark shall be understood as a spot on the video image that has distinct features. This can either be standard features (e.g. the tip of the nose that usually has a certain visual appearance) or it can be patient specific features (a black spot on the surface of the liver) that can be redetected in a subsequent video frame, but will not necessarily be found in any other patient.

BRIEF DESCRIPTION OF THE DRAWINGS

In the following, the invention is described with reference to the appended figures, which give background explanations and represent specific embodiments of the invention. The scope of the invention is however not limited to the specific features disclosed in the context of the figures, wherein FIG. 1 schematically shows a flow diagram of a computer-implemented method of generating an overlay of medical video data and overlay data according to an exemplary embodiment of the present invention.

DESCRIPTION OF EMBODIMENTS

Figure 1:
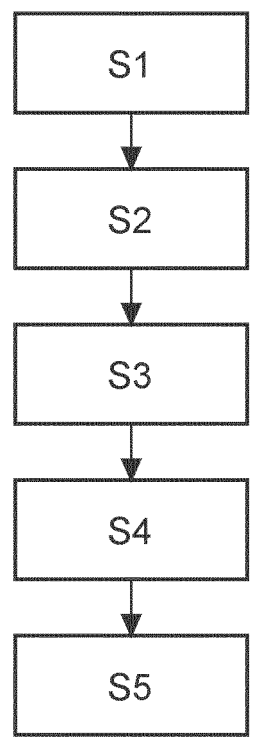

FIG. 1 schematically shows a flow diagram of a method that is computer-implemented and that generates an overlay of medical video data and overlay data to a user, in particular to a medical practitioner. The method comprises the step S1 in which the required medical video data are acquired from the used medical video modality. Said medical video data comprise at least a first video frame and a second video frame, which capture the image scene at different points in time t1 and t2. Moreover, in step S2, the acquired medical video data are analysed and said analysis comprises a comparison of the video data content captured by the first and the second video frames. As has been explained in detail hereinbefore and will be elucidated with embodiments hereinafter, such comparison of said at least two video frames can be carried out in several different ways. Moreover, the method shown in FIG. 1 comprises the provision of initial overlay data in step S3. Said provided initial overlay data can be an augmentation model, or can be overlay data that are received from an external system like for example a tracking system. Said initial overlay data are adapted in step S3 based on the result of the analysis/comparison of the medical video data that was carried out in step S3. In this way, modified overlay data are generated in step S4. Said generated modified overlay data are then used to generate the overlay, which is used as video output that is finally shown to the user.

Said overlay generated in step S5 comprises at least medical video data originating from the medical video modality and comprises the generated modified overlay data. Besides several different detailed embodiments of this method mentioned before, it is suggested to use two general mechanisms to analyse the acquired video data and correspondingly adapt the initial overlay data based on the result of said analysis. In a first general embodiment, extrapolation is used, which is for example further described in the context of the embodiment shown in FIG. 3. As a second mechanism, the inventors have found and suggest that the algorithm may wait with its decision whether and how to generate an overlay until the algorithm has read out a video frame of the video modality until a certain predefined maximum number of video frame pixels. When said video frame has been read out until this particular number of pixels, the algorithm can decide whether an augmentation, i.e., an overlay, shall be generated or not. This mechanism will be described in more detail with respect to the embodiments explained in the context of FIGS. 4 and 5.

It must be noted that the method shown in FIG. 1, as well as any other method embodiment described herein, can be carried out by for example device using an FPGA structure as is described in published patent application DE 10 2017 010 351 A1. In particular, a device described in FIG. 1 of said published patent application may be used for carrying out the present invention. The method of FIG. 1 disclosed herein can also be implemented into, for example, the technology known in connection with a system such as the one described in detail in DE 10 2017 010 351 A1. The device carrying out the method steps S1 to S5 described in FIG. 1 may have one or more processing units. Preferably, all components of such a device carrying out the present invention are provided within a semiconductor circuit within a single housing and comprises additionally FPGA blocks. As is clear to the skilled reader, such a device comprises the corresponding digital video inputs and/or digital video outputs. The device may also comprise an H264 and/or an H265 video encoder and video decoder in order to send and/or to receive video signals over network interfaces.

Figure 2:
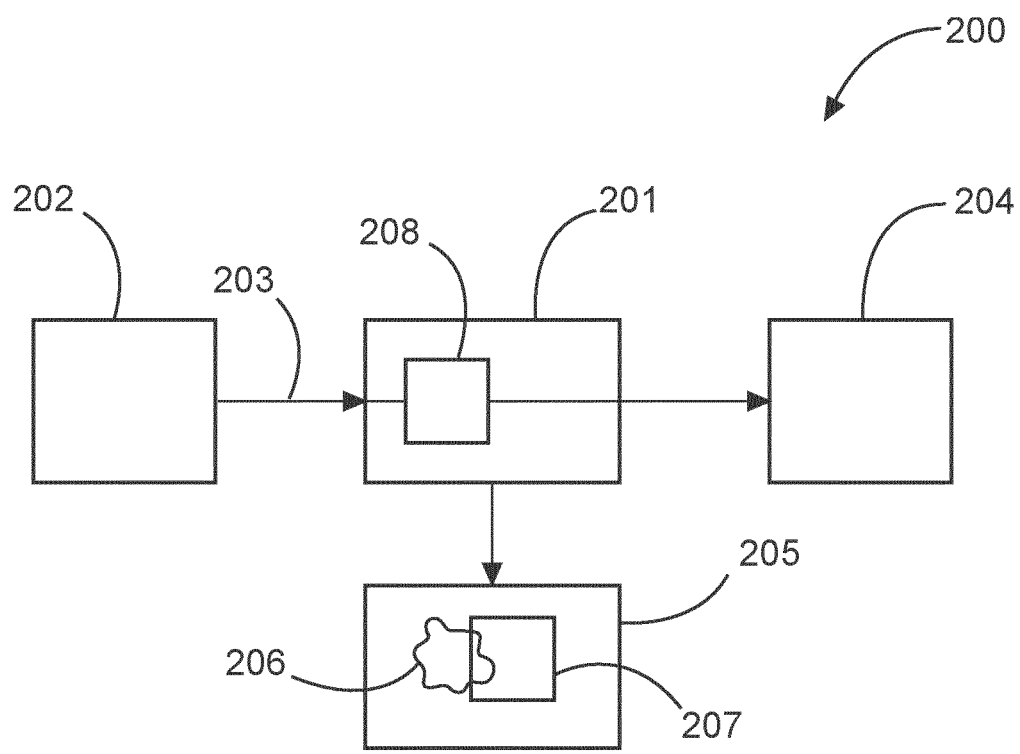
FIG. 2 schematically shows a medical video modality system according to another exemplary embodiment of the present invention.

FIG. 2 schematically shows a medical video modality system 200 comprising a computer 201, on which a program is running that causes the computer to perform the method steps as were explained for example with respect to previous FIG. 1. A processor/calculation unit 208 is comprised by the computer, which causes that steps S1 to S5, as were described hereinbefore and are described hereinafter in more detail, are carried out by the computer 201. The medical video modality system 200 further comprises imaging device 202, which generates the medical video data 203 that are provided to computer 201. In preferred embodiments, the imaging device 202 is embodied as an endoscope, an ultrasonic device, a microscope, or any combination thereof. The video signal 203 at least comprises the first and second video frames as mentioned herein. The video signal is provided to the storage unit 204 where it can be recorded. In addition, the video signal 203 is also forwarded to display 205 on which overlay comprising the modified overlay data can be presented together with video data to the user of the display 205 according to the present invention. As an exemplary embodiment, an anatomical object 206 can be seen on the screen 205 by the user, which is simultaneously displayed together with the augmentation model 207 being adapted as is disclosed herein.

The augmentation model may for example be an image and the corner points of the image are adapted, or the augmentation model may be a line model or a surface model (triangles and/or squares) and the nodes of this model are adapted. In another embodiment, a textured model, preferably using an additional transparency channel, could be newly rendered when adapting the augmentation model based on the result of the analysis of the first and second video frame, as has been explained hereinbefore in detail. In an embodiment, a so-called sweep line method is used in which the complexity of the model is reduced such that the maximum number of cross-sections of a line with the edges of the model do not exceed a particular and constant number that has been previously defined. The system carrying out the present invention may pre-order the data that are processed during the invention, preferably a pre-ordering in direction of the vertical axis of the image is used. As has been described before in detail, a stop or cancellation criterion could be defined such that no augmentation, i.e. no overlay generation, takes place when the detected movement is that significant that an augmentation would not provide fruitful results or would not be technically feasible.

Figure 3:
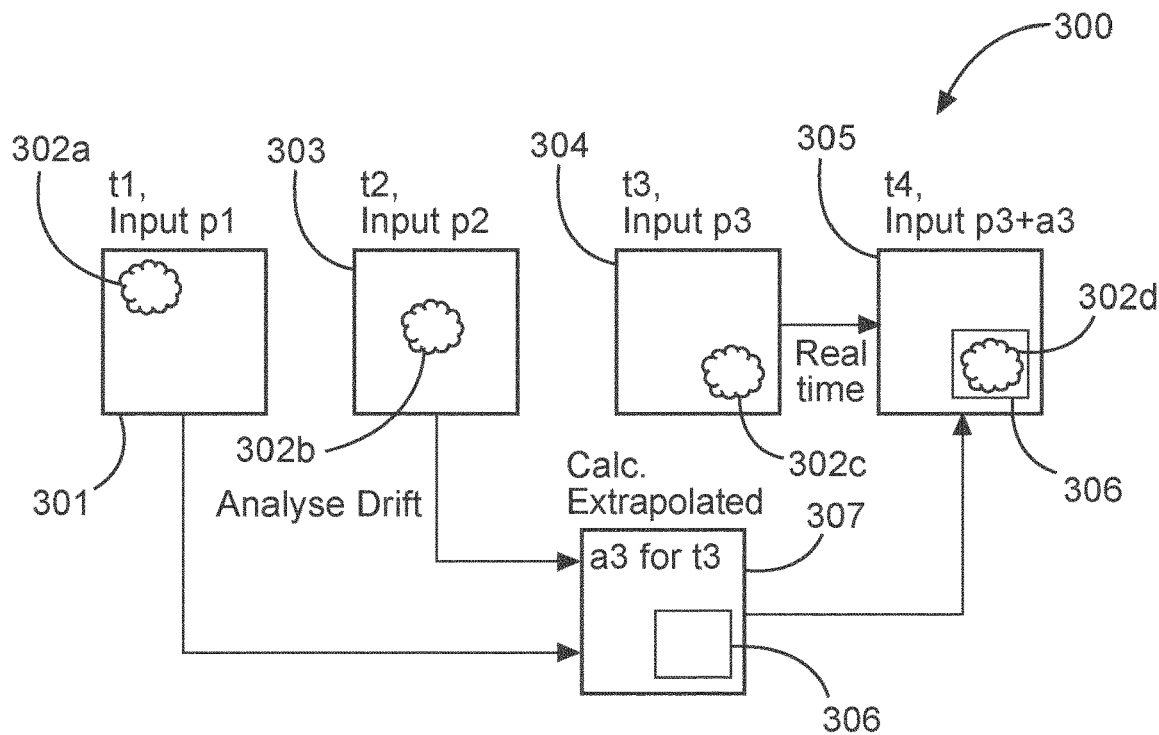
FIG. 3 schematically shows a flow diagram of another method embodiment, in which a drift detection is carried out and an extrapolation is calculated for an augmentation model according to another exemplary embodiment of the present invention.

FIG. 3 schematically shows a flow diagram 300 of another method embodiment, in which a drift detection is carried out and an extrapolation is calculated for an augmentation model according to another exemplary embodiment of the present invention. Also in the method 300 of FIG. 3 an overlay 305 of medical video data and overlay data is generated and the following steps are comprised. A first video frame 301 and a second video frame 303 of different points in time, t1 and t2, are acquired from a medical video modality, e.g. from a microscope. The acquired video data are automatically analysed by an algorithm determining a change over time in the medical video data of said two video frames 301 and 303 by comparing the first and second video frame. Moreover, in the method 300 shown in FIG. 3, at least a third video frame 304 is acquired from the microscope as medical video modality. The third video frame is from a third point in time t3. As can be seen in FIG. 3, all three video frames 301, 303 and 304 are provided as input p1, p2 and p3 for the processor, device or computer carrying out the method 300. As can be seen from illustrated anatomical object 302*a*, the position of the anatomical object in the second video frame 303 has changed to position 302*b*. Moreover, in video frame 304, the position of the anatomical object has changed to 302*c*. Thus, by comparing the first and the second video frame, the change in the video data can be determined, in the present case in the form of a drift analysis. In step 307, a calculation of an extrapolation of the initial overlay data is calculated to the point in time t3. Moreover, the video output 305 is generated which comprises the third video frame 304 as input p3 as well as the modified overlay data 306 that were generated by extrapolating the initial overlay data to the third point in time t3, which is shown in FIG. 3 with augmentation model 306. Therefore, by generating the video output 305, which is the desired overlay shown to the user, the medical practitioner is provided with a real-time augmentation in which the imaged object is shown at position 302*d* in combination with the real-time augmentation of augmentation model 306. In other words, the determined change over time in the first and second video frames 301 and 303 is a spatial shift of the object 302*a*, 302*b*, 302*c* and 302*d* imaged in the video frames. As is clear from the description of FIG. 3, the third video frame directly follows the second video frame in a video stream of the medical video modality. It should be noted that the drift analysis and the corresponding generation of an overlay as was described for FIG. 3, is used as an optional feature in the computer-implemented method 400 shown in the embodiment of FIG. 4 (see video frames 401 and 403 from t0 and t1).

Note that according to a similar embodiment developed further from the one described just before, the extrapolation of the initial overlay data is/are calculated to a fourth point in time t4. The generation of the video output here comprises the third video frame and the initial overlay data extrapolated to the fourth point in time t4. Moreover, between the third and fourth video frame from t3 and t4, a latency in time exists that is below one video frame, below one line of a video frame, or below 10, 8, 5 or below 4 pixels of a video frame of said video modality. In this embodiment using said "calculation to a fourth point in time t4", the augmentation model is extrapolated even more, since it takes into account an additional latency that is present between the video frame t3 and the generation of the overlay at t4. This latency is, however, below one video frame, or below one line of a video frame or below a few pixels of a video frame, Hence, the corresponding time in seconds that has to be added from t3 to t4, i.e. said very low latency mentioned just before, can be used for extrapolating the augmentation model/initial overlay data. The augmentation model extrapolated to t4 can then be beneficially displayed together with the video frame of t3 to the user.

It has been described before in detail for the embodiment shown in FIG. 3, that the initial overlay data are adapted by applying a spatial shift to the augmentation model. However, it is clear to the skilled practitioner that the generation of the modified overlay data may also comprise applying a distortion to the augmentation model, newly rendering the augmentation model, adapting at least one parameter of the augmentation model, replacing the augmentation model by another augmentation model or any combination thereof. In other words, in the embodiment shown in FIG. 3, an influence of the motion between the imaging device of the medical video modality and the image object is calculated and it is compensated for that calculated influence when generating the modified overlay data.

Figure 4:
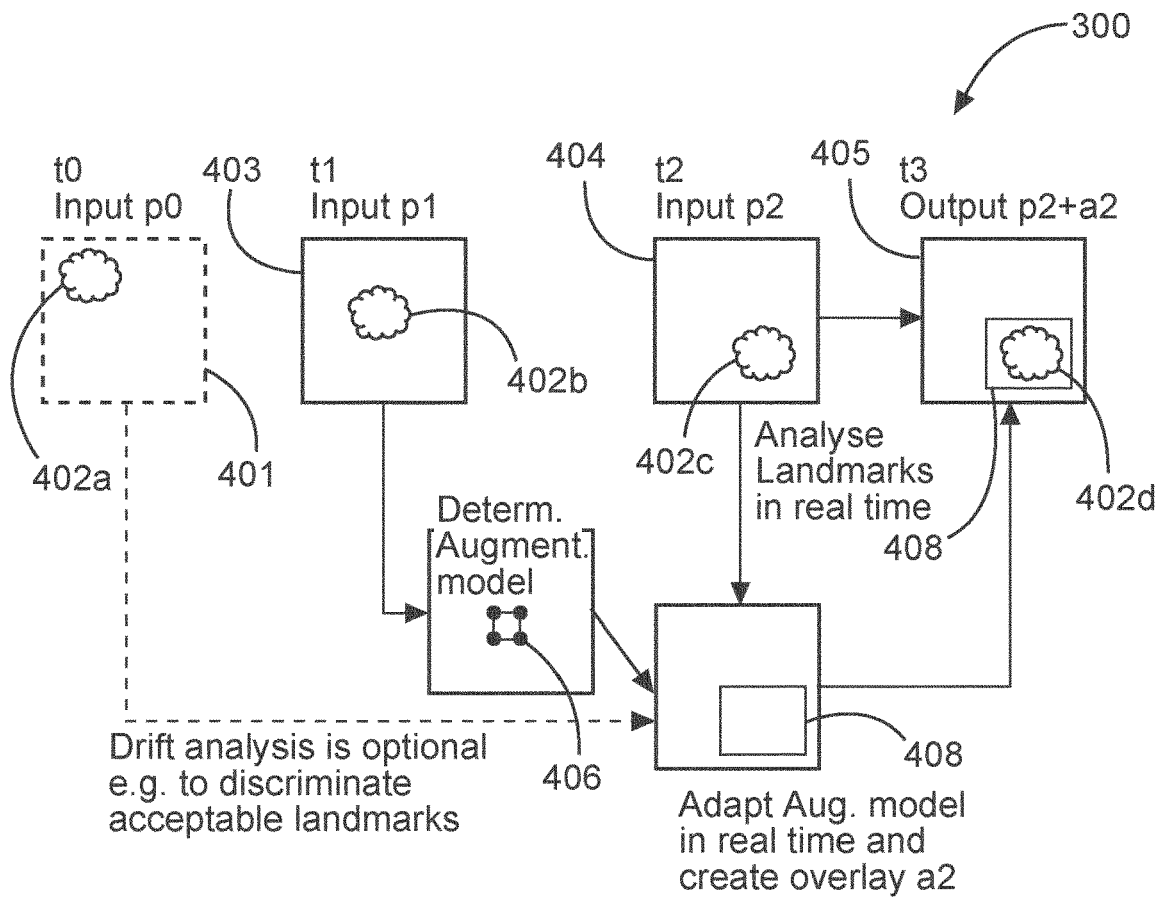
FIG. 4 schematically shows another method embodiment of the present invention in which a live adaption of the augmentation model is used.

FIG. 4 shows another method embodiment 400 of the computer-implemented method presented herein. In the method of FIG. 4, the first video frame 403 as well as the second video frame 404 are acquired from the medical video modality. They thus capture a scene at different points in time t1 and t2 and are used as input p1 and input p2 for the processor, computer or device carrying out the presented algorithm. As can be seen in FIG. 4 the augmentation model 406 is determined from the first video frame 403. Moreover, also at least one landmark of said augmentation model 406 is determined from the first video frame 403. While the processor, computer or device carrying out the presented algorithm is reading out the second video frame 404, it is automatically identified where said determined at least one landmark is present in the second video frame 404. Of course several landmarks can be used in the algorithm. Based on such an analysis of one or more landmarks in real-time, at least one parameter of the augmentation model 406 is adapted thereby generating the modified overlay data 408. The step of generating the overlay (as has been described hereinbefore e.g. in the context of FIG. 1 with step S5) comprises in this embodiment of FIG. 4 the following. The video output 405 generated by processor, computer or device carrying out the presented algorithm contains the second video frame 404 and the adapted augmentation model 408. Note that the landmark identification in frame 404 and the adaption of the at least one parameter of the initial augmentation model 406 are carried out simultaneously with the generation of the overlay 405 i.e. within the same video frame. The overlay 405 is then displayed to a user. The adapted augmentation model 408 is added pixel-wise output a2 to p2, which is video content of the second video frame 404 while scanning at t2 the second video frame 404, i.e. a real-time overlay. As can be gathered from FIG. 4, see the left-hand side, an optional drift analysis can be used for example in order to discriminate acceptable landmarks. For this purpose, an earlier video frame 402 showing object 402a and originating from point in time t0 may be provided as input p0. The drift analysis aspect shown in FIG. 4 is similar to what has been described hereinbefore, e.g. in the context of FIG. 3.

Figure 5:
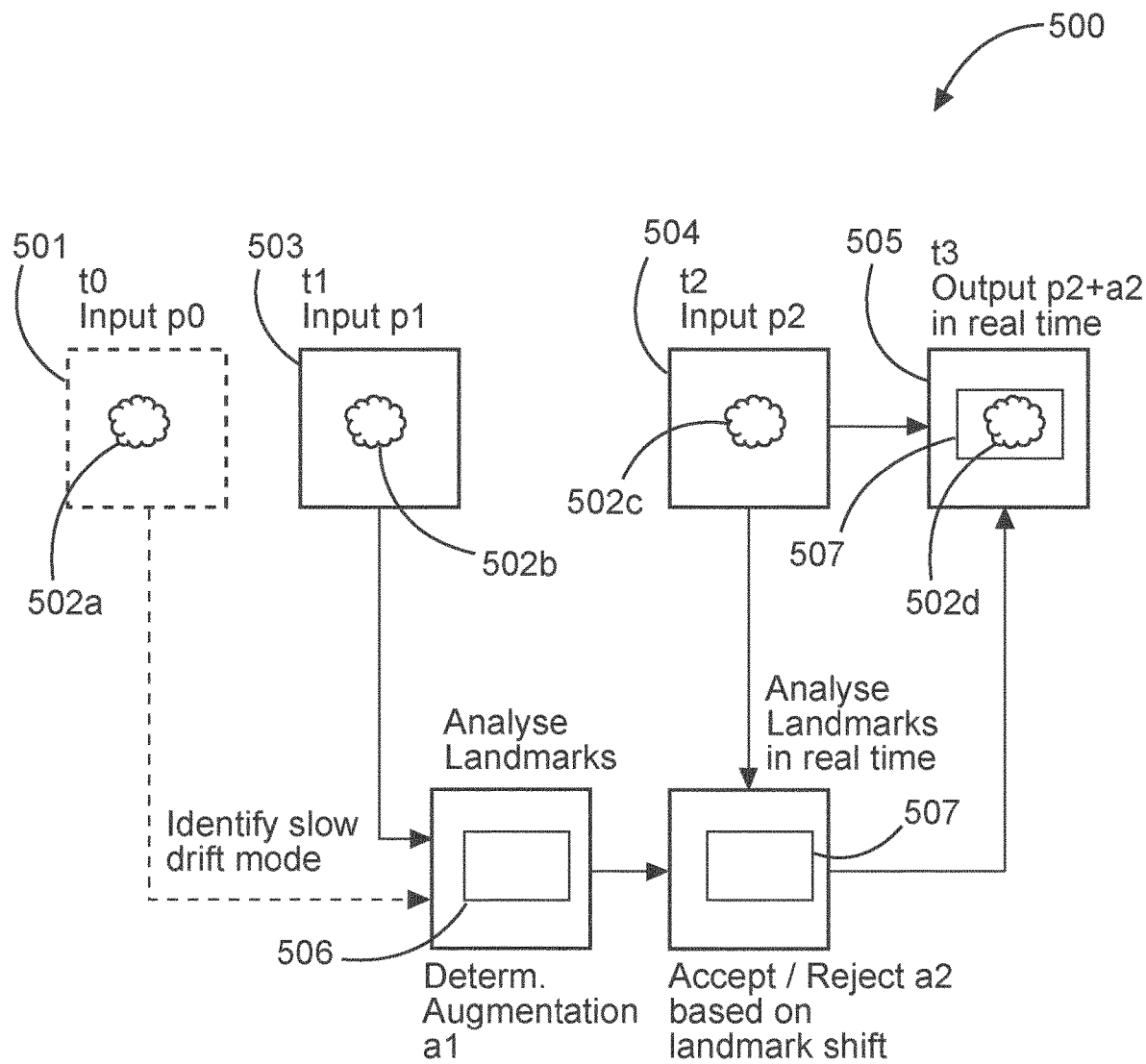
FIG. 5 schematically shows a method embodiment of the present invention in which the overlay, i.e. the augmentation, is carried out depending on a detected drift velocity or depending on the detected position of landmarks.

In addition to the embodiments of FIG. 3 and FIG. 4, FIG. 5 shows another computer-implemented method according to a further embodiment 500 of the present invention. In the method 500 of FIG. 5, a spatial drift of an object 502a, 502b and 502c imaged by the medical video modality is determined by analysing at least the two video frames 501 and 503, which originate from points in time before the second video frame 504 was captured. In the embodiment 500, it is decided based on the determined amount of spatial shift, whether a landmark is accepted to be used in the method and/or whether the overlay 505 is generated. In other words, it is evaluated in method 500 whether a particular landmark determined in the video frame 503 is present in the video frame 504 within a pre-defined maximum number of video frame pixels thereby using a line-wise video frame read-out. And no overlay is generated if said particular landmark is not present in the video frame 504 within said maximum number of video frame pixels. Moreover, similar to FIG. 4, the initial augmentation model 506 is determined based on the analysis of landmarks in the first video frame 503. Based on the identified drift it can be decided whether the adapted augmentation model 507 is accepted or rejected based on the landmark shift detected. In case it is accepted, described as "accept a2 based on landmark shift" in FIG. 5, the overlay 505 is generated by combining the video content p2 as output together with the generated modified overlay data 507, i.e. modified augmentation model 507, which is shown to the user overlaid to anatomical object 502d in FIG. 5. The algorithm 500 described in FIG. 5 can beneficially generate the overlay 505 as a real time overlay having a latency in time compared to the medical video data of below one video frame, or even below a few pixels. In this scenario, the shift might be down a few lines equating to tens of thousands of pixels (still being very small).

Furthermore, the terms "first", "second", "third" or "(a)", "(b)", "(c)", "(d)" or "(i)", "(ii)", "(iii)", "(iv)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(a)", "(b)", "(c)", "(d)" or "(i)", "(ii)", "(iii)", "(iv)" etc. relate to steps of a method or use or assay there is no time or time interval coherence between the steps unless indicated otherwise, i.e. the steps may be carried out simultaneously or there may be time intervals of seconds, minutes, hours, days, weeks, months or even years between such steps, unless otherwise indicated in the application as set forth herein above or below.

Other variations to the disclosed embodiments can be understood and effected by those skilled in the art in practicing the claimed invention, from the study of the drawings, the disclosure, and the appended claims. In the claims the word "comprising" does not exclude other elements or steps and the indefinite article "a" or "an" does not exclude a plurality. A single processor or other unit may fulfill the functions of several items or steps recited in the claims. The mere fact that certain measures are recited in mutually different dependent claims does not indicate that a combination of these measures cannot be used to advantage. A computer program may be stored/distributed on a suitable medium such as an optical storage medium or a solid-state medium supplied together with or as part of other hardware, but may also be distributed in other forms, such as via the Internet or other wired or wireless telecommunication systems. Any reference signs in the claims should not be construed as limiting the scope of the claims.

The invention claimed is:

1. A computer-implemented method of generating an overlay of medical video data and overlay data, comprising:
    acquiring, from a medical video modality, the medical video data comprising at least a first video frame and a second video frame of different points in time, t1 and t2;
    analysing the acquired medical video data comprising a comparison of the video data captured by the first and the second video frames;
    providing initial overlay data;
    generating modified overlay data by adapting the initial overlay data based on a result of the analysis of the medical video data; and
    generating the overlay by generating a video output comprising at least medical video data originating from the medical video modality and including the generated modified overlay data
    determining from the first video frame an augmentation model;
    determining from the first video frame at least one landmark of said augmentation model;
    automatically identifying the determined at least one landmark in the second video frame while reading out the second video frame;
    adapting at least one parameter of the augmentation model based on a result of the landmark identification in the second video frame, thereby generating the modified overlay data;
    wherein the step of generating the overlay includes:
    generating the video output comprising the second video frame and the adapted augmentation model; and
    wherein the landmark identification and the adaption of the at least one parameter of the augmentation model are carried out simultaneously, i.e. within the same video frame, with the generation of the overlay.

2. The method of claim 1,
    wherein the generated overlay is a real time overlay characterized in that it has a latency in time compared to the medical video data of below one video frame, below five lines of a video frame, below two lines of a video frame, below one line of a video frame, below twenty pixels of a video frame, below ten pixels of a video frame, below eight pixels of a video frame, below five pixels of a video frame, or below four pixels of a video frame.

3. The method of claim 1,
    wherein the initial overlay data is an augmentation model, and
    wherein the generation of the modified overlay data includes at least one of applying a spatial shift to the augmentation model, applying a distortion to the augmentation model, newly rendering the augmentation model, adapting parameters of the augmentation model, replacing the augmentation model by another augmentation model, and any combination thereof.

4. The method of claim 1 further including:
    calculating an influence of a motion between an imaging device of the medical video modality and the imaged object and compensating for said calculated influence when generating the modified overlay data.

5. The method of claim 1,
    wherein the comparison of the video data captured by the first and the second video frames is embodied as automatically determining a landmark of an augmentation model in the first video frame and as searching and finding the determined landmark in the second video frame.

6. The method of claim 1;
    wherein the generation of the overlay is carried out simultaneously.

7. The method of claim 1,
    wherein the step of landmark identification comprises:
    evaluating whether a particular landmark determined in the first video frame is present in the second video frame within a pre-defined maximum number of video frame pixels thereby using a line-wise video frame read-out; and
    wherein no overlay is generated if said particular landmark is not present in the second video frame within the maximum number of video frame pixels.

8. The method of claim 1, further comprising:
    determining a spatial drift of an object imaged by the medical video modality by analysing at least two video frames of the video modality from points in time before the second video frame was captured, and
    deciding, based on the determined spatial drift, whether a landmark is accepted to be used in the method and/or whether the overlay is generated.

9. The method of claim 1 further comprising:
    automatically identifying a particular instrument in the first video frame; and
    acquiring an augmentation model of said identified particular instrument from a database thereby providing the initial overlay data.

10. The method of claim 1,
    wherein the step of analysing the acquired medical video data comprises determining a change in the medical video data over time by comparing the first and second video frame and further comprising:
    acquiring, from the medical video modality, at least a third video frame of a third point in time t3;
    wherein the step of generating the modified overlay data includes:
    using the determined change in the video data of the first and second video frames over time in a calculation of an extrapolation of the initial overlay data to the point in time; and
    wherein the generation of the overlay includes:
    generating the video output including the third video frame and the initial overlay data that were extrapolated to the third point in time t3.

11. The method of claim 10;
    wherein the following relation holds true: t1<t2<t3; and
    wherein the third video frame directly follows the second video frame in a video stream of the medical video modality.

12. The method of claim 10:
    wherein the determined change over time in the first and second video frames is a spatial shift of an object imaged in the video frames.

13. A non-transitory computer readable media comprising instructions which, when executed by one or more processors, causes the one or more processors to:

acquire, from a medical video modality, the medical video data comprising at least a first video frame and a second video frame of different points in time, t1 and t2;
analyse the acquired medical video data comprising a comparison of the video data captured by the first and the second video frames;
provide initial overlay data;
generate modified overlay data by adapting the initial overlay data based on a result of the analysis of the medical video data; and
generate the overlay by generating a video output comprising at least medical video data originating from the medical video modality and including the generated modified overlay data
determining from the first video frame an augmentation model;
determining from the first video frame at least one landmark of said augmentation model;
automatically identifying the determined at least one landmark in the second video frame while reading out the second video frame;
adapting at least one parameter of the augmentation model based on a result of the landmark identification in the second video frame, thereby generating the modified overlay data;
wherein the step of generating the overlay includes:
generating the video output comprising the second video frame and the adapted augmentation model; and
wherein the landmark identification and the adaption of the at least one parameter of the augmentation model are carried out simultaneously, i.e. within the same video frame, with the generation of the overlay.

14. A medical video modality system comprising:
at least one processor and associated memory having instructions which when executed cause the at least one processor to:
acquire, from a medical video modality, the medical video data comprising at least a first video frame and a second video frame of different points in time, t1 and t2;
analyse the acquired medical video data comprising a comparison of the video data captured by the first and the second video frames;
provide initial overlay data;
generate modified overlay data by adapting the initial overlay data based on a result of the analysis of the medical video data; and
generate the overlay by generating a video output comprising at least medical video data originating from the medical video modality and including the generated modified overlay data
an imaging device for generating the medical video data;
determining from the first video frame an augmentation model;
determining from the first video frame at least one landmark of said augmentation model;
automatically identifying the determined at least one landmark in the second video frame while reading out the second video frame;
adapting at least one parameter of the augmentation model based on a result of the landmark identification in the second video frame, thereby generating the modified overlay data;
wherein the step of generating the overlay includes:
generating the video output comprising the second video frame and the adapted augmentation model, and
wherein the landmark identification and the adaption of the at least one parameter of the augmentation model are carried out simultaneously, i.e. within the same video frame, with the generation of the overlay.

15. The medical video modality system of claim 14, wherein the imaging device is an endoscope, an ultrasonic device, a microscope, or any combination thereof.

* * * * *